United States Patent [19]

Fassina

[11] Patent Number: 4,889,121
[45] Date of Patent: Dec. 26, 1989

[54] PAIN-RELIEVING COMPOSITE HAVING A RELATIVELY RAPID ACTION

[76] Inventor: Antonio Fassina, Via S. Marco, 26, Milano, Italy

[21] Appl. No.: 6,177

[22] Filed: Jan. 23, 1987

Related U.S. Application Data

[63] Continuation-in-part of Ser. No. 817,562, Jan. 10, 1986, abandoned.

[51] Int. Cl.$^4$ .............................................. A61N 5/06
[52] U.S. Cl. ...................................... 128/381; 63/12; 128/380; 128/395; 350/407
[58] Field of Search ............... 128/379, 380, 381, 395, 128/396; 63/12, 13, 14.1–14.8; 350/406, 407

[56] References Cited

U.S. PATENT DOCUMENTS 2,304,504 12/1942 Metzger et al. ..................... 350/407
2,699,706 1/1955 Boone ......................... 350/406 U X
2,715,315 8/1955 Giardini .......................... 128/381 X
3,474,255 10/1969 White ................................. 350/407
4,587,957 5/1986 Castel .................................. 128/1.3
4,686,986 8/1987 Fenyo et al. ........................ 128/396

FOREIGN PATENT DOCUMENTS 8151 of 1892 United Kingdom ................ 128/380

Primary Examiner—Anton O. Oechsle
Attorney, Agent, or Firm—Ostrolenk, Faber, Gerb & Soffen

[57] ABSTRACT

An orientable composite having application to the human body for the relief of pain is provided. The composite consist of at least one pair of polarizing plates having polarization axes perpendicular to one another and the bisecting lines of the angles formed by said polarization axes coincide with the longitudinal axes of the body part of the painful area to be treated.

5 Claims, 3 Drawing Sheets

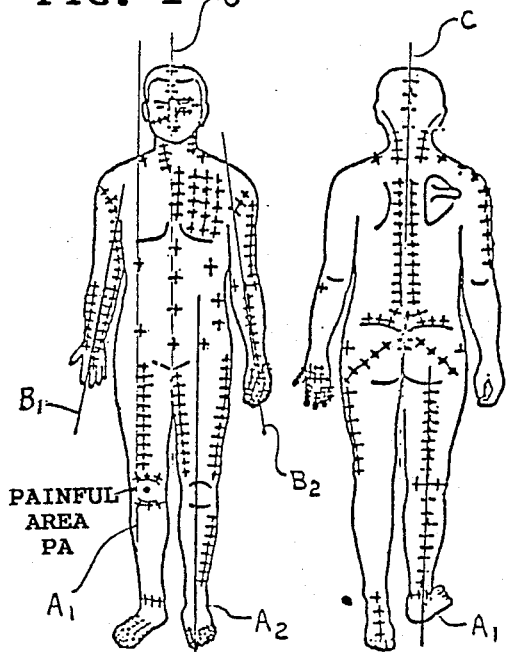
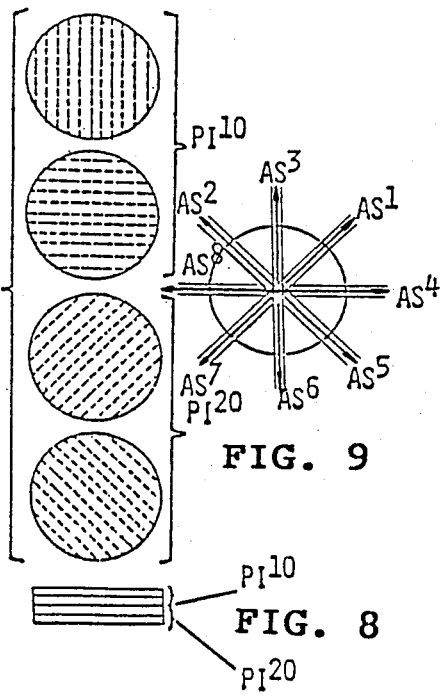
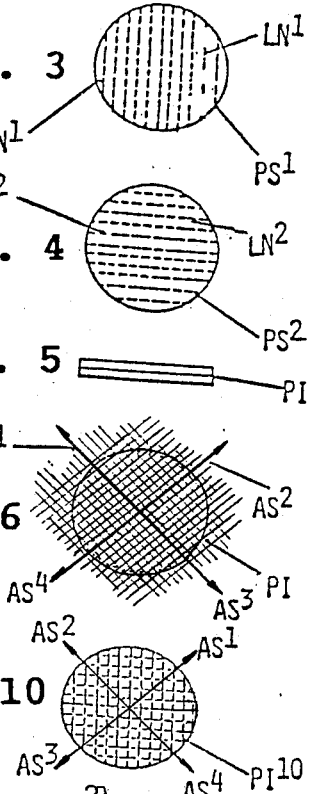
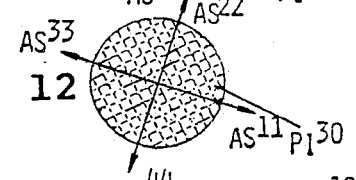
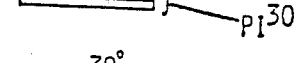
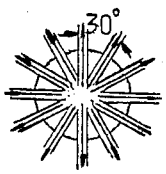

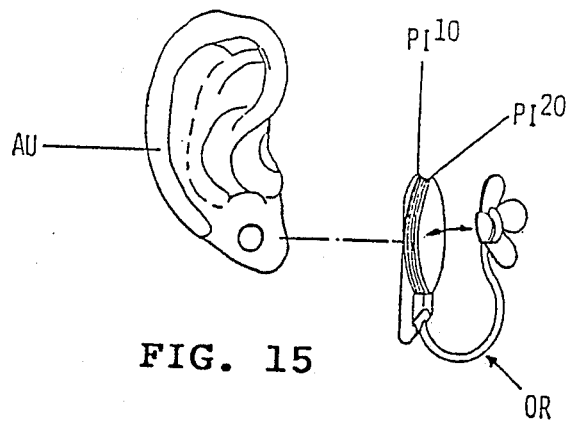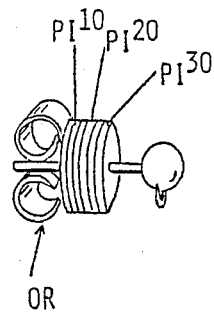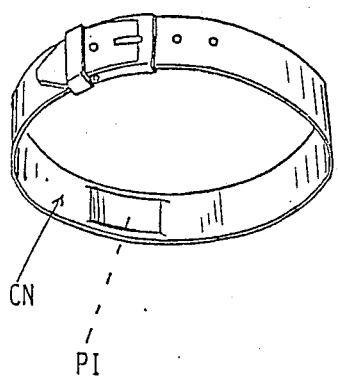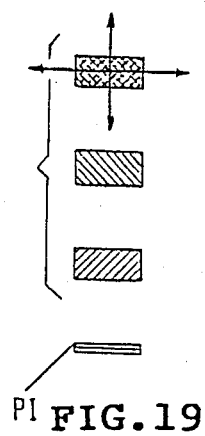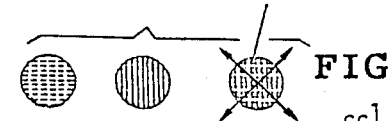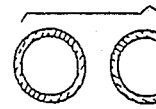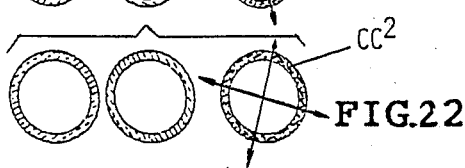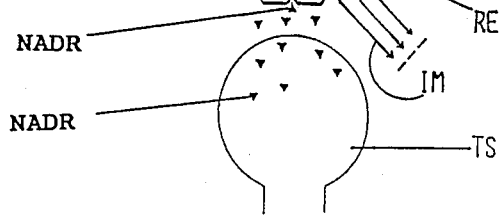

PAIN-RELIEVING COMPOSITE HAVING A RELATIVELY RAPID ACTION

This application is a continuation-in-part of applicant's copending application Ser. No. 817,562, filed Jan. 10, 1986, abandoned.

The present invention relates to a pain-relieving composite comprised of two polarizing plates oriented at 90° to one another and which exhibit a relatively rapid action.

A detailed study of the mode of action of devices of this type (as will be more fully described hereinafter) has shown that such devices can produce a strong as well as relatively rapid pain-relieving effect if applied directly to the site of the pain. Also, the pain-relieving action is found to be maximized if the active axes defined by the bisecting lines of the angles formed by the polarization axes of the plates coincide with the longitudinal axes of the body part on which the painful area is located (See $A_1A_2$, $B_1B_2$, C of FIG. 26).

According to the present invention there is provided a pain-relieving composite having a relatively rapid action characterized in that it comprises at least one pair of polarizing plates or elementary composite, the plates being oriented such that their polarization axes are perpendicular to each other. This composite is orientable, the bisecting lines of said angles being orthogonal to each other according to the longitudinal axis of the painful area to be treated.

In practice, it is rather difficult to orient "ad hoc" the active axes of the composite precisely bearing in mind that the composite is usually applied by the patient himself.

Accordingly it is preferred that the composite possess at least eight active axes, wherein it is provided in association with a movable support to be applied to the skin whereby the maximum deviation from the optimum axis of one of the active axes is $360/(2n \times 2)$ where n is the number of polarizing plates. When n=4 this deviation is 22° 30', which deviation can be considered almost negligible.

Since the active axes of the "elementary composite" must be in alignment to the longitudinal axis of the body part to be treated in order to obtain the maximal analgesic effect there are only two positions, orthogonal to each other, in which the maximal analgesic effect results when the composite consists of only two polarizing plates (See $AA_1$, $BB_1$ of FIG. 26 and $BB_1$, $AA_1$ of FIG. 27). Apart from these two positions the analgesic effect is progressively reduced, being still present at 22° 30' but absent at the 45° deviation (See FIG. 28). Accordingly, it is preferred that the composite be formed by two "elementary composites" (four polarizing plates) oriented at 45° to each other in order to obtain four maximal analgesic positions.

If, for convenience only the central active axes of each "elementary composite" is drawn then there is obtained the configuration shown in FIGS. 29 and 30 and the "complex composite" of FIG. 31 which is characterized by 4 active axes ($AA_1$, $A_2A_3$, $BB_1$, $B_2B_3$). With such a "complex composite" there are four positions in which the maximal analgesic effect results. Apart from these four positions the analgesic effect is still present (even if somewhat reduced), being the maximal deviation from the active axes 22° 30'.

In practice, if a patient orients an "elementary composite" in a position where the analgesic effect is very poor, a "complex composite" (having a deviation from an active axis which is practically negligible, i.e., 22° 30'), can be employed by the patient to find a position where the analgesic effect can be achieved.

The present invention will now be described by reference to the accompanying drawings.

THE DRAWINGS

FIGS. 1 and 2 show some points of the human body where the composite of the present invention should be applied in order to obtain a maximum pain-relieving effect.

FIGS. 3, 4, 5 and 6 show, respectively, two polarizing plates with their polarization axes perpendicular to each other, an elementary composite (FIG. 5) formed from the two plates as seen in vertical elevation and the same elementary composite as seen in plan with the active axes oriented at 90° to each other (FIG. 6).

FIG. 7 shows an exploded view of a "complex composite" formed from four polarizing plates, the first two plates and the last two plates constituting an "elementary composite" as shown in FIG. 6, but with the two elementary composites being angularly offset with respect to their active axes by 45° in order to generate active axes oriented in sequence at 45° to each other.

FIGS. 8 and 9, respectively, represent in vertical elevation and in plan the composite of FIG. 7 with its active axes.

FIGS. 10, 11 and 12 show three elementary composites, as illustrated in FIG. 5, wherein each one is fixed with respect to the other, but oriented at an angle of 30° to each other.

FIG. 13 shows in elevation a composite formed from the elementary composites of FIGS. 10 to 12.

FIG. 14 shows in plan the active axes of the composite of FIG. 13.

FIGS. 15 and 16 show in perspective two earrings to be fastened to a lobe of an ear AU, each earring comprising a pain-relieving composite as shown in FIGS. 8 and 13, respectively.

FIGS. 17, 18 and 19 show, respectively, a perspective view of a pain-relieving wrist band (FIG. 17) incorporating a composite of the invention, an exploded view (FIG. 18) of a composite as shown in FIGS. 3 to 6 adapted to fit such a wrist band, and, in elevation (FIG. 19) the complete composite of FIG. 18.

FIGS. 20, 21, 22, 23 and 24 illustrate a variation of the composite of FIGS. 10 to 14 in the form of an internal disc and two concentric rings.

FIG. 25 illustrates a hypothesis explaining a possible principle of operation of the disclosed invention.

Figures 26, 27, 28:
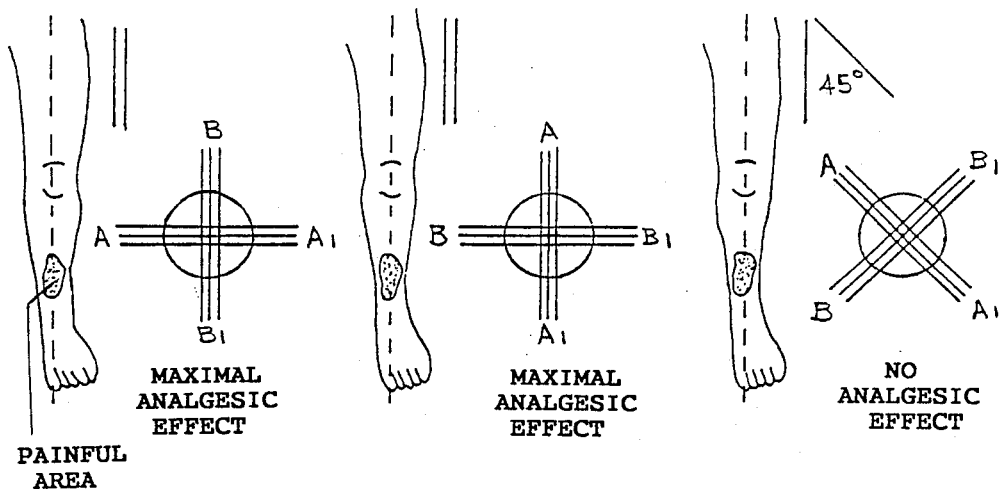

FIGS. 26-28 illustrate composites formed by the positioning of two polarizing plates according to this invention.

Figures 29, 30, 31:
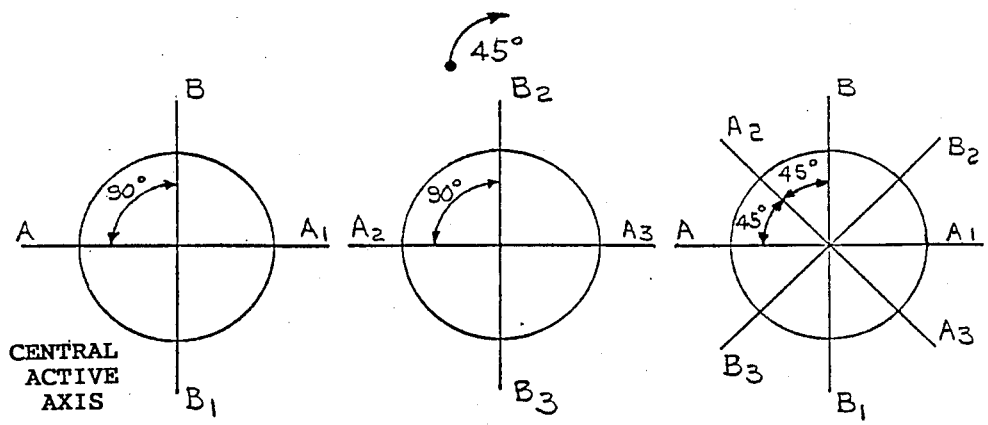

FIGS. 29-31 illustrate complex composites having four active axes arranged according to this invention.

DESCRIPTION OF THE PREFERRED EMBODIMENTS

In FIGS. 3-6 there are shown two plates $PS^1$ and $PS^2$ in the form of small discs, the plates being made of a polarizing material, desirably a film of Polaroid (trademark) material, with the polarization axes $LN^1$ and $LN^2$ being perpendicular to each other, whereby, on superimposition of the plates to form a composite PI as shown in FIG. 5 the active axes such as $AS^1$, $AS^2$, $AS^3$ and $AS^4$ thereof are formed from the bisecting lines of the angles formed by the polarization axes such as $LN^1$-$LN^2$ of the two superimposed plates.

For maximum effect, the composite should be oriented so that one of its active axes such as ($AS^1$-$AS^4$) coincides as closely as possible with the longitudinals of the body part where the painful area is located. Such an axis is indicated by $A_1$ for the painful area PA of FIG. 1. If a wrist band CN is used to alleviate a wrist pain (See FIG. 17) no orientation problem exists since the composite used in such a wrist band, e.g. that of FIG. 5, is held by the wrist band in a fixed orientation and thus can be pre-set in order to obtain maximum effect.

The polarizing material may be cut into any suitable shape e.g. discs, squares or rectangles. Conveniently, the diameter of each disc is about 10 mm. with a plate thickness of from 0.2-0.7 mm. The transmittance of each plate may vary from 10% to 40% or more.

Practical tests have shown that if one of the illustrated composites is applied to any painful point of the body and if the composite is so oriented that one of its active axes is orthopaedically oriented with the longitudinal axis of the body part (as defined with reference to FIGS. 1 and 2) a relatively rapid relief of the pain is obtained. It has been found that the same effect may be obtained by using a composite where superimposed polarizing plates surround, rather than overlie each other, as shown for example in FIGS. 20 to 24 where an inner disc DI is surrounded by two concentric rings $CC^1$ and $CC^2$. To better comprehend this effect reference is made to FIGS. 10-14 where active axes are provided and the concentric composite is analogous to that of FIGS. 20-24. Since the active life of each polarizing plate, and hence the resulting composite, is believed to be unlimited, the composites of the invention may be incorporated into an adhesive tape system so that each composite can be used not just once but many times.

As will be clear from the foregoing, when a composite according to FIGS. 3 to 6 is used the maximum deviation from its optimum orientation is $360/(2n \times 2)$, where n is the number of plates, which in this case is two, so that the maximum deviation is $360/(2 \times 2 \times 2) = 45°$.

According to a further aspect of this invention, instead of two plates as described above, four plates can be used in the form of two pairs of plates $PI^{10}$ and $PI^{20}$, each pair PI being as shown in FIG. 5, but with the pair $PI^{20}$ being oriented at 45° to the pair $PI^{10}$. In this case, a complex composite is obtained wherein its active axes are disposed at 45° to each other and, therefore, the maximum deviation for the composite of FIGS. 8 and 9 is 22° 30′ since n in the formula $360/(2n \times 2)$ is now 4.

If it is desired to decrease this deviation still further, three pairs of plates $PI^{10}$, $PI^{20}$, and $PI^{30}$ can be used as shown in FIGS. 10 to 14, each pair being off-set by 30° so that the active axes as such $AS^1$-$AS^4$; $AS^{10}$-$AS^{40}$; $AS^{11}$-$AS^{44}$ are similarly disposed at 30° to each other. In this case n in the formula $360/(2n \times 2)$ is 6 giving a deviation of 15°.

Although for general application on adhesive tape-based system is desirable, any mode of application of the described composites to the human body is possible. The adhesive may have the active axes of the composite printed thereon. In FIGS. 15 and 16, for example, composites of the types shown in FIGS. 8 and 13 can be incorporated into an earring for affixing to the lobe AU of an ear for use in so-called ear therapy.

There now follows a brief discussion of the possible mode of pain-relieving action effected by the composites of the present invention.

The mode of operation for the described composites is based on the principle that a hormone of the sympathetic nervous system, noradrenaline (Nadr), is involved in the sensing of pain. Pain impulses arise, in the presence of Nadr, from peripheral pain receptors (nociceptors) and run through afferent sensitive nerves towards the cortex.

Under normal conditions (normal discharge threshold of the nociceptor and normal amount of Nadr) pain impulses do not arise. When pain occurs the pain impulses arise because of one of the following situations:
(1) normal discharge threshold of the nociceptor in the presence of an increased amount of Nadr (sympathetic hypertone);
(2) lowered discharge threshold of the nociceptor in the presence of a normal amount of Nadr (sympathetic normotone).

Because of the presence of the composite of the invention a raising of the discharge threshold of the receptors is believed to take place, whereby, the pain impulses from receptors in either conditions 1 or 2 above are not initiated by the endogenous Nadr locally present.

The operation of the above hypothesis is illustrated in FIG. 25 wherein TS shows a sympathetic terminal where Nadr is the noradrenaline, RE is the pain receptor, PI is the composite of the invention oriented as described above, CU represents the skin and IM the pain impulses. From this figure it is apparent that the pain sensations are decreased by the presence of the composite PI because the locally-present Nadr causes no discharge from the receptor since its discharge threshold has been raised because of the presence of the composite PI. It is generally accepted by the scientific community that Nadr is a mediator for the sensation of pain and it is on the basis of this hypothesis that the raising of the discharge threshold of receptors in the presence of Nadr at any point of the human body causes a decrease in the perceived sensation of pain.

The described hypothesis is supported by the observation that for a number of conditions for which patients have been successfully treated with a sympathetic regional block with guanethidine (this being a known sympathicolytic drug used for pain relief in the treatment of e.g. Sudeck's disease) as reported in the following medical works: Mc KAY NNS, WOODHOUSE NJY, CLARKE AK. "Post-traumatic reflex sympathetic dystrophy syndrone (Sudeck's atrophy): effects of regional guanethidine infusion and salmon calcitonin"; British Medical Journal 2, 1575-6, 1977; LOH L, NATHAN PW, "Painful peripheral states and sympathetic blocks"; Journal of Neurology, Neurosangery and Phychiatry 41, 664, 1978); causalgia (as reported in the following medical works: HANNINGTON-KIFF JG, "Relief of causalgia in limbs by regional intravenous guanethidine"; British Medical Journal 2, 367-8, 1979 and LOH L, NATHAN PW, "Painful peripheral states and sympathetic blocks" Journal of Neurology, Neurosungery and Psychiatry 41, 664, 1978) and experimentally, for sciatic algosyndromes (as reported in the following medical works: FASSINA A., "Sciatic pain due to herniated disc and regional sympathetic block"; Archive of Orthopaedia and Rheumatalgia 97, 157-62, 1984); similar effects have also been observed after the application of composites of the invention to the appropriate regions of the body.

In particular, the inventor has observed that in patients suffering from sciatic pain in one of the lower limbs a significant decrease in the isometric strength of the extensor muscles of the wrist on the same side was present, e.g. right sciatica-right wrist. Muscle testings must be performed with the technique described by the applied kinesiology as reported in the following medical works: LARSON D. "Physical balancing: acupuncture and applied kinesiology"; American Journal of Acupuncture 13, 159–62, 1985.

The inventor has observed that the guanethidine block which achieves relief of the sciatic pain in these patients also produces a clear, although temporary (3–4 days) renewal of the strength of the wrist extension. This effect of increased strength together with pain relief has also been verified in the same patients as a result of the simple application of some of the composites according to the invention as described above at various points of the foot and leg.

It may thus be concluded that the described composites have a mode of action similar to that of a guanethidine block, but most probably not by removing Nadr (since a block requires at least 10 minutes), but by raising relatively rapidly the receptor discharge threshold in the cutaneous zones lying immediately thereunder.

The logical inference of these results is that upon application of the composites of the present invention to any part of the body a relatively rapid relief of topical pain is achieved by virtue of the raising of the discharge threshold of Nadr of the receptors locally present.

The activity of the described composites is considered to be based upon the solar radiation that passes through the atmosphere to the earth's surface.

Electromagnetic emanations from the sun comprise a wide range of radiation and include electric waves, radio waves, infrared rays, visible light, ultraviolet light, roentgen rays, gamma rays and secondary cosmic rays. Approximately 50 percent of the radiant energy emitted by the sun is present in the visible portion of the spectrum (380 to 720 nm), about 40 percent in the infrared region and about 10 percent in the ultraviolet region. Infrared rays exert a thermic effect and have wavelengths of 720 to 3140 nm.

Spectral analysis of the composite shows that it strongly absorbs visible light and ultraviolet light so that there is practically no transmittance in this region. On the other hand, a fairly good transmittance is present in the region of the first infrared between 800 and 2200 nm. In this range, the light which emerges from the composite is polarized, and this condition can be verified by a spectral analysis issued by the University of Milan.

What is claimed is:

1. A pain-relieving composite having a relatively rapid action for application to a body part having a longitudinal axis and a painful area, comprising at least two pairs of superposed plates of polarizing material, each pair having its plates oriented such that their polarization axes are perpendicular to each other, each bisecting line of the angles formed by the polarization axes constituting an active axis of the composite, the plates being oriented so that each plate has an active axis which is angularly offset with respect to the active axis of an adjacent plate by about 45° so as to provide at least one of the active axes in a position substantially coinciding with the longitudinal axis of the body part in which the painful area is located to provide relief to the painful area.

2. A composite as claimed in claim 1, wherein the composite is adapted to be mounted on a movable support to be applied to skin of the body part, the composite having a maximum deviation between the longitudinal axis and one of the active axes defined as (360°)/(4n), wherein n is the number of pairs of polarizing plates in the composite.

3. A composite as claimed in claim 1, wherein the composite comprises six plates, each plate being angularly offset with respect to an adjacent plate by 30° so as to provide six active axes, the composite having a maximum deviation between the longitudinal axes and one of the active axes of about 15°.

4. A composite as claimed in claim 2, wherein the composite forms part of a wrist band.

5. A composite as claimed in claim 1, wherein the maximum deviation of one of the active axes to the longitudinal axis, however the composite is applied to the body part, is about 22° 30′.

* * * * *